US009144631B2

(12) United States Patent
Asius et al.

(10) Patent No.: US 9,144,631 B2
(45) Date of Patent: Sep. 29, 2015

(54) CERAMIC-BASED INJECTABLE IMPLANTS WHICH ARE USED TO FILL WRINKLES, CUTANEOUS DEPRESSIONS AND SCARS, AND PREPARATION METHOD THEREOF

(75) Inventors: Jerome Asius, Baillargues (FR); Benedicte Asius, Baillargues (FR)

(73) Assignees: Benedicte Asius, Baillargues (FR); Jerome Asius, Baillargues (FR); Nicolas Riviere, Villeneuve les Avignon (FR); Jean-Michel Bord, Pierrelatte (FR)

( * ) Notice: Subject to any disclaimer, the term of this patent is extended or adjusted under 35 U.S.C. 154(b) by 2839 days.

(21) Appl. No.: 10/542,544

(22) PCT Filed: Jan. 27, 2004

(86) PCT No.: PCT/FR2004/000180
§ 371 (c)(1),
(2), (4) Date: Jul. 18, 2005

(87) PCT Pub. No.: WO2004/069090
PCT Pub. Date: Aug. 19, 2004

(65) Prior Publication Data
US 2006/0094871 A1 May 4, 2006

(30) Foreign Application Priority Data

Jan. 27, 2003 (FR) ...................... 03 00853

(51) Int. Cl.
| A61F 13/00 | (2006.01) |
| A61F 2/00 | (2006.01) |
| C08B 37/00 | (2006.01) |
| A61L 27/58 | (2006.01) |
| A61L 27/12 | (2006.01) |
| A61L 27/46 | (2006.01) |
| A61L 27/50 | (2006.01) |

(52) U.S. Cl.
CPC ............... *A61L 27/58* (2013.01); *A61F 2/0059* (2013.01); *A61L 27/12* (2013.01); *A61L 27/46* (2013.01); *A61L 27/50* (2013.01); *A61L 2400/06* (2013.01)

(58) Field of Classification Search
CPC .......... A61L 27/58; A61L 27/12; A61L 27/46
See application file for complete search history.

(56) References Cited

U.S. PATENT DOCUMENTS

| 4,191,747 A | 3/1980 | Scheicher |
| 4,309,488 A | 1/1982 | Heide et al. |
| 4,373,217 A * | 2/1983 | Draenert .................... 623/23.62 |
| 4,619,655 A | 10/1986 | Hanker et al. |
| 4,643,982 A | 2/1987 | Kasuga et al. |
| 4,657,548 A | 4/1987 | Nichols |
| 4,693,986 A | 9/1987 | Vit et al. |
| 4,772,287 A | 9/1988 | Ray et al. |
| 4,803,075 A | 2/1989 | Wallace et al. |
| 4,820,306 A | 4/1989 | Gorman et al. |
| 4,837,285 A | 6/1989 | Berg et al. |
| 4,839,215 A | 6/1989 | Starling et al. |
| 4,842,603 A | 6/1989 | Draenert |
| 4,851,046 A | 7/1989 | Low et al. |
| 4,880,610 A | 11/1989 | Constantz |
| 4,904,260 A | 2/1990 | Ray et al. |
| 5,007,940 A | 4/1991 | Berg |
| 5,047,031 A | 9/1991 | Constantz |
| 5,053,212 A | 10/1991 | Constantz et al. |
| 5,085,861 A | 2/1992 | Gerhart et al. |
| 5,116,387 A | 5/1992 | Berg |
| 5,129,905 A | 7/1992 | Constantz |
| 5,162,430 A | 11/1992 | Rhee et al. |
| 5,178,845 A | 1/1993 | Constantz et al. |
| 5,204,382 A | 4/1993 | Wallace et al. |
| 5,258,028 A | 11/1993 | Ersek et al. |
| 5,264,214 A | 11/1993 | Rhee et al. |
| 5,273,964 A | 12/1993 | Lemons |
| 5,292,802 A | 3/1994 | Rhee et al. |
| 5,304,595 A | 4/1994 | Rhee et al. |
| 5,306,500 A | 4/1994 | Rhee et al. |
| 5,306,673 A | 4/1994 | Hermansson |
| 5,308,889 A | 5/1994 | Rhee et al. |
| 5,324,775 A | 6/1994 | Rhee et al. |
| 5,328,955 A | 7/1994 | Rhee et al. |

(Continued)

FOREIGN PATENT DOCUMENTS

| DE | 3941023 | 6/1990 |
| EP | 0 196 143 A2 | 1/1986 |

(Continued)

OTHER PUBLICATIONS

Article of J. Biomed Mater Res. Feb. 2000; 49(2):176-82':. Dissolution of dense carbonate apatite subcutaneously implanted in Wistar rats, by J. Barralet, M. Akao, H. Aoki, H. Aoki.

(Continued)

*Primary Examiner* — Tigabu Kassa
(74) *Attorney, Agent, or Firm* — Young & Thompson

(57) ABSTRACT

The invention relates to implants which are based on a biodegradable thixotropic compound having pseudoplastic properties and which can be injected subcutaneously or intradermally into the fibrous tissue. The inventive implant comprises microparticles of at least one biocompatible ceramic compound which are suspended in a vector fluid containing at least one hyaluronic acid-based compound and at least one biodegradable thixotropic compound having pseudoplastic properties. The invention also relates to a kit for the extemporaneous use of such implants, the production of said implants and the use thereof in order to fill wrinkles and/or fine lines and/or cutaneous depressions and/or scars.

52 Claims, No Drawings

(56) References Cited

U.S. PATENT DOCUMENTS

| | | |
|---|---|---|
| 5,336,263 A | 8/1994 | Ersek et al. |
| 5,336,264 A | 8/1994 | Constanz et al. |
| 5,338,772 A | 8/1994 | Bauer et al. |
| 5,344,452 A | 9/1994 | Lemperle |
| 5,352,715 A | 10/1994 | Wallace et al. |
| 5,356,629 A | 10/1994 | Sander et al. |
| 5,376,375 A | 12/1994 | Rhee et al. |
| 5,413,791 A | 5/1995 | Rhee et al. |
| 5,433,751 A | 7/1995 | Christel et al. |
| 5,446,091 A | 8/1995 | Rhee et al. |
| 5,470,911 A | 11/1995 | Rhee et al. |
| 5,475,052 A | 12/1995 | Rhee et al. |
| 5,476,666 A | 12/1995 | Rhee et al. |
| 5,480,644 A | 1/1996 | Freed |
| 5,510,121 A | 4/1996 | Rhee et al. |
| 5,510,418 A | 4/1996 | Rhee et al. |
| 5,522,896 A | 6/1996 | Prescott |
| 5,523,291 A | 6/1996 | Janzen et al. |
| 5,523,348 A | 6/1996 | Rhee et al. |
| 5,527,856 A | 6/1996 | Rhee et al. |
| 5,531,786 A | 7/1996 | Perry et al. |
| 5,543,441 A | 8/1996 | Rhee et al. |
| 5,550,187 A | 8/1996 | Rhee et al. |
| 5,550,188 A | 8/1996 | Rhee et al. |
| 5,565,519 A | 10/1996 | Rhee et al. |
| 5,571,182 A | 11/1996 | Ersek et al. |
| 5,614,221 A | 3/1997 | Fjellstrom |
| 5,614,587 A | 3/1997 | Rhee et al. |
| 5,618,549 A | 4/1997 | Patat et al. |
| 5,633,001 A * | 5/1997 | Agerup ............... 424/423 |
| 5,643,464 A | 7/1997 | Rhee et al. |
| 5,650,176 A | 7/1997 | Lee et al. |
| 5,662,708 A | 9/1997 | Hayes et al. |
| 5,667,778 A | 9/1997 | Atala |
| 5,676,976 A | 10/1997 | Lee et al. |
| 5,681,873 A | 10/1997 | Norton et al. |
| 5,683,461 A | 11/1997 | Lee et al. |
| 5,702,677 A | 12/1997 | Shimp et al. |
| 5,711,957 A | 1/1998 | Patat et al. |
| 5,717,006 A | 2/1998 | Daculsi et al. |
| 5,744,545 A | 4/1998 | Rhee et al. |
| 5,782,971 A | 7/1998 | Constantz et al. |
| 5,786,421 A | 7/1998 | Rhee et al. |
| 5,800,541 A | 9/1998 | Rhee et al. |
| 5,820,632 A | 10/1998 | Constantz et al. |
| 5,840,290 A | 11/1998 | Hench et al. |
| 5,866,610 A | 2/1999 | Lang et al. |
| 5,900,254 A | 5/1999 | Constantz |
| 5,922,025 A | 7/1999 | Hubbard |
| 5,936,035 A | 8/1999 | Rhee et al. |
| 5,952,010 A | 9/1999 | Constantz |
| 5,962,028 A | 10/1999 | Constantz |
| 5,997,574 A | 12/1999 | Hayes et al. |
| 6,001,394 A | 12/1999 | Daculsi et al. |
| 6,002,065 A | 12/1999 | Constantz et al. |
| 6,005,162 A | 12/1999 | Constantz |
| 6,027,742 A | 2/2000 | Lee et al. |
| 6,037,519 A | 3/2000 | McKay |
| 6,051,247 A | 4/2000 | Hench et al. |
| 6,117,456 A | 9/2000 | Lee et al. |
| 6,132,463 A | 10/2000 | Lee et al. |
| 6,139,578 A | 10/2000 | Lee et al. |
| 6,214,368 B1 | 4/2001 | Lee et al. |
| 6,277,151 B1 | 8/2001 | Lee et al. |
| 6,287,341 B1 | 9/2001 | Lee et al. |
| 6,288,043 B1 | 9/2001 | Spiro et al. |
| 6,306,418 B1 | 10/2001 | Bley |
| 6,323,146 B1 | 11/2001 | Pugh et al. |
| 6,331,312 B1 | 12/2001 | Lee et al. |
| 6,346,123 B1 | 2/2002 | McKay |
| 6,383,519 B1 | 5/2002 | Sapieszko et al. |
| 6,417,247 B1 | 7/2002 | Armstrong et al. |
| 6,432,437 B1 | 8/2002 | Hubbard |
| 6,440,427 B1 | 8/2002 | Wadstrom |
| 6,451,059 B1 * | 9/2002 | Janas et al. ............... 623/23.51 |
| 6,485,754 B1 | 11/2002 | Wenz et al. |
| 6,495,156 B2 | 12/2002 | Wenz et al. |
| 6,521,246 B2 | 2/2003 | Sapieszko et al. |
| 6,537,574 B1 | 3/2003 | Hubbard |
| 6,537,589 B1 | 3/2003 | Chae et al. |
| 6,541,037 B1 | 4/2003 | Lee et al. |
| 6,544,290 B1 | 4/2003 | Lee et al. |
| 6,558,612 B1 | 5/2003 | Hubbard |
| 6,585,992 B2 | 7/2003 | Pugh et al. |
| 6,685,963 B1 | 2/2004 | Taupin et al. |
| 6,689,375 B1 | 2/2004 | Wahlig et al. |
| 6,793,725 B2 | 9/2004 | Chow et al. |
| 6,831,172 B1 | 12/2004 | Barbucci et al. |
| 6,846,493 B2 | 1/2005 | Pugh et al. |
| 6,903,146 B2 | 6/2005 | Matsushima et al. |
| 6,921,819 B2 | 7/2005 | Piron et al. |
| 6,923,989 B2 | 8/2005 | Lacout et al. |
| 6,943,154 B2 | 9/2005 | Miller et al. |
| 6,949,251 B2 | 9/2005 | Dalal et al. |
| 6,953,594 B2 | 10/2005 | Lee et al. |
| 6,972,130 B2 | 12/2005 | Lee et al. |
| 6,991,803 B2 | 1/2006 | Sapieszko et al. |
| 7,004,974 B1 | 2/2006 | Larsson et al. |
| 7,019,192 B2 * | 3/2006 | Gertzman et al. ......... 623/16.11 |
| 7,060,287 B1 * | 6/2006 | Hubbard et al. ............... 424/423 |
| 7,087,745 B1 | 8/2006 | Pallado et al. |
| 7,150,879 B1 | 12/2006 | Lee et al. |
| 7,223,420 B2 | 5/2007 | Berger et al. |
| 7,226,620 B2 | 6/2007 | Hendricks et al. |
| 7,294,187 B2 | 11/2007 | Chow et al. |
| 7,316,882 B2 | 1/2008 | Katagiri et al. |
| 2001/0053938 A1 | 12/2001 | Dorigatti et al. |
| 2002/0018796 A1 | 2/2002 | Wironen |
| 2002/0076429 A1 | 6/2002 | Wironen et al. |
| 2002/0098222 A1 | 7/2002 | Wironen et al. |
| 2002/0136696 A1 | 9/2002 | Lee et al. |
| 2002/0151466 A1 | 10/2002 | Hubbard et al. |
| 2002/0155137 A1 | 10/2002 | Lee et al. |
| 2002/0155167 A1 | 10/2002 | Lee et al. |
| 2003/0049328 A1 | 3/2003 | Dalal et al. |
| 2003/0055512 A1 | 3/2003 | Genin et al. |
| 2003/0082232 A1 | 5/2003 | Lee et al. |
| 2003/0157178 A1 | 8/2003 | Chen et al. |
| 2003/0158302 A1 | 8/2003 | Chaput et al. |
| 2003/0170289 A1 | 9/2003 | Chen et al. |
| 2003/0180364 A1 | 9/2003 | Chen et al. |
| 2003/0199615 A1 | 10/2003 | Chaput et al. |
| 2004/0024069 A1 | 2/2004 | Chen et al. |
| 2004/0030341 A1 | 2/2004 | Aeschlimann et al. |
| 2004/0037810 A1 | 2/2004 | Von Heimburg et al. |
| 2004/0047912 A1 | 3/2004 | Bardonnet et al. |
| 2004/0048947 A1 | 3/2004 | Lidgren et al. |
| 2004/0076685 A1 | 4/2004 | Tas |
| 2004/0185021 A1 | 9/2004 | Hubbard |
| 2004/0244651 A1 | 12/2004 | Lemaitre et al. |
| 2005/0031704 A1 | 2/2005 | Ahn |
| 2005/0084537 A1 | 4/2005 | Martyn et al. |
| 2005/0100581 A1 | 5/2005 | Laurencin et al. |
| 2005/0124720 A1 | 6/2005 | Rizzoli et al. |
| 2005/0170012 A1 | 8/2005 | Dalal et al. |
| 2005/0209704 A1 | 9/2005 | Maspero et al. |
| 2005/0226936 A1 | 10/2005 | Agerup |
| 2006/0029571 A1 | 2/2006 | Karageozian et al. |
| 2006/0039951 A1 | 2/2006 | Sapieszko et al. |
| 2006/0073182 A1 | 4/2006 | Wong et al. |
| 2006/0122706 A1 | 6/2006 | Lo |
| 2006/0141040 A1 | 6/2006 | Chen et al. |
| 2006/0165663 A1 | 7/2006 | Tanaka et al. |
| 2006/0173551 A1 | 8/2006 | Hubbard et al. |
| 2006/0194758 A1 | 8/2006 | Lebreton |
| 2006/0211982 A1 | 9/2006 | Prestrelski et al. |
| 2006/0240121 A1 | 10/2006 | Lee et al. |
| 2006/0257358 A1 | 11/2006 | Wen et al. |
| 2006/0263443 A1 | 11/2006 | Chow et al. |
| 2006/0292198 A1 | 12/2006 | Dalal et al. |
| 2007/0003505 A1 | 1/2007 | Carey |
| 2007/0003593 A1 | 1/2007 | Wironen et al. |
| 2007/0041906 A1 | 2/2007 | Lidgren et al. |
| 2007/0098736 A1 | 5/2007 | Cleland et al. |

(56) References Cited

U.S. PATENT DOCUMENTS

| | | |
|---|---|---|
| 2007/0184035 A1 | 8/2007 | Pugh et al. |
| 2007/0184087 A1 | 8/2007 | Voigts et al. |
| 2007/0196415 A1 | 8/2007 | Chen et al. |
| 2007/0212385 A1 | 9/2007 | David |
| 2007/0259181 A1 | 11/2007 | Furuzono et al. |
| 2007/0265622 A1 | 11/2007 | Aeschlimann et al. |
| 2007/0270974 A1 | 11/2007 | Aeschlimann et al. |

FOREIGN PATENT DOCUMENTS

| | | |
|---|---|---|
| EP | 0259484 | 9/1987 |
| EP | 0310623 | 12/1987 |
| EP | 0251695 | 1/1988 |
| EP | 0298501 | 1/1989 |
| EP | 0304305 B1 | 2/1989 |
| EP | 0347028 | 12/1989 |
| EP | 0353936 B1 | 2/1990 |
| EP | 0406375 | 6/1990 |
| EP | 0416761 | 3/1991 |
| EP | 0429419 | 5/1991 |
| EP | 0444157 B1 | 9/1991 |
| EP | 0541687 | 2/1992 |
| EP | 0497846 B1 | 8/1992 |
| EP | 0590015 | 12/1992 |
| EP | 0522569 | 1/1993 |
| EP | 0648239 | 1/1994 |
| EP | 0612723 | 8/1994 |
| EP | 0622990 B1 | 11/1994 |
| EP | 0649309 | 11/1994 |
| EP | 0650374 | 11/1994 |
| EP | 0 627 899 B1 | 12/1994 |
| EP | 0631499 B1 | 1/1995 |
| EP | 0640647 | 3/1995 |
| EP | 0656214 | 6/1995 |
| EP | 0656215 | 6/1995 |
| EP | 0692986 | 8/1995 |
| EP | 0680990 | 11/1995 |
| EP | 0697218 | 2/1996 |
| EP | 0825963 | 11/1996 |
| EP | 0747066 | 12/1996 |
| EP | 0843562 | 2/1997 |
| EP | 0850029 | 2/1997 |
| EP | 0847376 | 3/1997 |
| EP | 0835668 | 4/1998 |
| EP | 0934087 | 4/1998 |
| EP | 0941079 | 4/1998 |
| EP | 0984797 | 9/1998 |
| EP | 1009333 | 1/1999 |
| EP | 0910546 B1 | 4/1999 |
| EP | 0936929 B1 | 8/1999 |
| EP | 1051205 | 8/1999 |
| EP | 0973561 B1 | 1/2000 |
| EP | 1091775 | 1/2000 |
| EP | 1094851 | 2/2000 |
| EP | 1117381 | 3/2000 |
| EP | 1150659 | 7/2000 |
| EP | 1169387 | 10/2000 |
| EP | 1187636 | 12/2000 |
| EP | 1204434 | 2/2001 |
| EP | 1 080 698 A1 | 3/2001 |
| EP | 1080699 B1 | 3/2001 |
| EP | 1080737 B1 | 3/2001 |
| EP | 1220690 | 4/2001 |
| EP | 1229858 | 5/2001 |
| EP | 1120439 B1 | 8/2001 |
| EP | 1259271 | 9/2001 |
| EP | 1144459 B1 | 10/2001 |
| EP | 1272232 | 10/2001 |
| EP | 1153621 | 11/2001 |
| EP | 1301219 | 1/2002 |
| EP | 1303542 | 1/2002 |
| EP | 1355981 | 7/2002 |
| EP | 1227851 B1 | 8/2002 |
| EP | 1237585 B1 | 9/2002 |
| EP | 1363543 | 9/2002 |
| EP | 1372748 | 9/2002 |
| EP | 1255576 B1 | 11/2002 |
| EP | 1399111 | 12/2002 |
| EP | 1280562 B1 | 2/2003 |
| EP | 1443981 | 5/2003 |
| EP | 1446099 | 5/2003 |
| EP | 1446100 | 5/2003 |
| EP | 1446101 | 5/2003 |
| EP | 1450765 | 7/2003 |
| EP | 1344538 | 9/2003 |
| EP | 1490123 | 10/2003 |
| EP | 1380313 | 1/2004 |
| EP | 1532291 | 3/2004 |
| EP | 1413320 | 4/2004 |
| EP | 1545466 | 4/2004 |
| EP | 1589901 | 7/2004 |
| EP | 0784487 | 9/2004 |
| EP | 1611160 | 10/2004 |
| EP | 1622656 | 11/2004 |
| EP | 1622843 | 11/2004 |
| EP | 1482996 | 12/2004 |
| EP | 1660036 | 4/2005 |
| EP | 1535633 | 6/2005 |
| EP | 1715829 | 8/2005 |
| EP | 1734894 | 10/2005 |
| EP | 1746884 | 11/2005 |
| EP | 1755556 | 11/2005 |
| EP | 1601387 | 12/2005 |
| EP | 1793803 | 4/2006 |
| EP | 1830809 | 7/2006 |
| EP | 1787954 | 5/2007 |
| EP | 1808411 | 7/2007 |
| EP | 1865002 | 12/2007 |
| EP | 1526835 | 4/2008 |
| FR | 2693716 | 1/1994 |
| FR | 2705235 | 11/1994 |
| FR | 2715853 | 8/1995 |
| FR | 2733426 | 10/1996 |
| FR | 2733427 | 10/1996 |
| FR | 2737663 | 2/1997 |
| FR | 2778336 | 11/1999 |
| FR | 2780730 | 1/2000 |
| FR | 2794763 | 12/2000 |
| FR | 2805747 | 9/2001 |
| FR | 2805748 | 9/2001 |
| FR | 2811996 | 1/2002 |
| FR | 2819722 | 7/2002 |
| FR | 2819814 | 7/2002 |
| FR | 2824272 | 11/2002 |
| FR | 2825924 | 12/2002 |
| FR | 2852249 | 9/2004 |
| GB | 2227176 | 7/1990 |
| GB | 2377642 | 1/2003 |
| JP | 63317159 | 12/1988 |
| JP | 3094761 | 4/1991 |
| JP | 3-196834 A | 8/1991 |
| JP | 2002058736 | 2/2002 |
| JP | 2004181121 | 7/2004 |
| NL | 8304129 | 7/1985 |
| WO | 8704110 | 7/1987 |
| WO | WO-87/05521 | 9/1987 |
| WO | 8707495 | 12/1987 |
| WO | 8806873 | 9/1988 |
| WO | WO-91/17777 A1 | 11/1991 |
| WO | WO-93/15721 | 8/1993 |
| WO | 9316658 | 9/1993 |
| WO | 9316711 | 9/1993 |
| WO | 9317075 | 9/1993 |
| WO | 9317976 | 9/1993 |
| WO | WO-93/16657 | 9/1993 |
| WO | 9402184 | 2/1994 |
| WO | WO-94/21299 | 9/1994 |
| WO | 9426283 | 11/1994 |
| WO | 9621427 | 7/1996 |
| WO | WO-97/05832 | 2/1997 |
| WO | 9806873 | 2/1998 |
| WO | WO-98/17330 | 4/1998 |
| WO | WO-98/40113 | 9/1998 |

(56) References Cited

FOREIGN PATENT DOCUMENTS

| | | |
|---|---|---|
| WO | WO-98/56431 | 12/1998 |
| WO | WO-99/02107 | 1/1999 |
| WO | WO-99/19003 | 4/1999 |
| WO | 9924070 | 5/1999 |
| WO | WO-99/38543 | 8/1999 |
| WO | WO-9951164 | 10/1999 |
| WO | WO-00/78356 | 12/2000 |
| WO | WO-01/12247 A1 | 2/2001 |
| WO | WO-01/28591 | 4/2001 |
| WO | WO-01/74410 | 10/2001 |
| WO | WO-02/05861 | 1/2002 |
| WO | WO-02/062721 | 8/2002 |
| WO | WO-02/069817 | 9/2002 |
| WO | WO-03/041684 | 5/2003 |
| WO | WO-03/041685 | 5/2003 |
| WO | WO-03/041753 | 5/2003 |
| WO | WO-2004012703 | 2/2004 |
| WO | WO-2004078223 | 9/2004 |
| WO | WO-2004092222 | 10/2004 |
| WO | WO-2004093734 | 11/2004 |

OTHER PUBLICATIONS

Search Report issued in FR 03 00 853 application by the French Patent Office on Oct. 10, 2003.

PCT International Search Report issued in PCT/FR2004/000180 dated Aug. 23, 2004.

Notice of Reasons for Rejection dated Jun. 14, 2010, and dispatched Jun. 16, 2010, in corresponding Japanese Patent Application No. 2006-502122 (with full English translation).

\* cited by examiner

CERAMIC-BASED INJECTABLE IMPLANTS WHICH ARE USED TO FILL WRINKLES, CUTANEOUS DEPRESSIONS AND SCARS, AND PREPARATION METHOD THEREOF

BACKGROUND OF THE DISCLOSURE

The invention relates to implants for subcutaneous or intradermal injection into fibrous tissue, for use in man or animals in reparatory or plastic surgery or in esthetic dermatology for filling wrinkles, fine lines, skin depressions and scars, including the filling of skin defects secondary to the taking of a treatment liable to result in a lipodystrophy usually characterized by facial lipoatrophy.

A certain number of products have been used to date. Each product has advantages and disadvantages.

Silicone oils, which are banned as injections, were easy to use. However, migration of droplets of silicone into the tissues located below the point of injection, by simple gravity, has been observed after injection. Silicone incorrectly used or used in large amount has been the cause of siliconoma, and even of delayed allergic reactions. Silicone is not biodegradable.

Teflon® paste is a suspension of polytetrafluoroethylene microparticles (diameter from 10 to 100 μm) in glycerol. This product, in many cases, caused severe and chronic serous infections and had to be removed after a few months from the dermal and subdermal tissues for the majority of patients. It has also been proven that small polytetrafluoroethylene microparticles were found in the liver.

Collagen suspensions have been very widely used in the last ten years. Collagen has remained the leader in these indications for a very long time since it was virtually the only product used that benefits from a marketing authorization for the treatment of aging of the skin. A few cases of allergic reactions have been noted in about 3% of patients. The resorption of collagen occurs on average in the majority of patients between 3 and 5 months, which necessitates several injections per year in order to have a certain level of efficacy. Finally, it should be noted that collagen is of bovine origin.

Biological samples taken from the patient himself. The idea was, admittedly, interesting, but the clinical experience revealed the failure in reimplanting fatty cells, which are absorbed and disappear within a few weeks. Another system consisted in adding plasma from the patient to a collagen gelatin of bovine and porcine origins. The results are even more disappointing and the product is of animal origin.

Hyaluronic acid used in the majority of pharmaceutical forms or in the majority of medical devices is in the form of a sodium hyaluronate gel. It is, very widely used by virtue of its ease of injection and its safety of use, and it offers a good alternative on account of its biocompatibility and its absence of toxicity. These sodium hyaluronate gels are moreover widely used in eye surgery. However, their rapid bioresorbability (typically ranging between 4 and 6 months) may disappoint certain users in the field of filling wrinkles or skin depressions, since the injections must be repeated at close and regular intervals.

Bioplastics are polymerized silicone microparticles (diameter 70 to 140μ) dispersed in poly-vinylpyrrolidone. Rejection reactions have been noted.

Polymethyl methacrylate (PMMA) microspheres 20 to 40 μm in diameter in suspension either in a gelatin solution or in a collagen solution or in a hyaluronic acid solution. PMMA is not biodegradable, although widely used in the field of ophthalmology in the form of an intraocular implant. In the dermato-esthetic field, there is not sufficient history to know how this implant behaves after five or six years of intradermal implantation. Moreover, when the vector is a collagen solution (of bovine origin), allergy has been reported in 3% of cases.

Polylactic acid (PLA) microparticles of poly-morphic form and from 40 to 63 μm in diameter in suspension in sodium carmellose. The product sold under the name Newfill® represents advantageous progress since it allows efficacy of treatment over a relatively long period, limiting the injection sessions. The polymer used is an L PLA 100 (crystalline form of 100% levorotatory PLA) that incurs extremely slow resorption kinetics (more than 5 years). However, the persistence of PLA crystals in the tissues may be feared, which may, in certain cases, lead in the long term to chronic inflammatory reactions during repeated injections. The use of CMC (cellulose derivative) may, on the one hand, be the cause of allergic reactions, and, on the other hand, the body does not have an enzymatic system capable of degrading cellulose. Furthermore, extemporaneous reconstitution, vigorous shaking for homogenization before use, and poor syringeability of the product limit its use and put off many users. Cases of granuloma at two years and also cystic nodules requiring exeresis in the majority of cases are beginning to be reported.

FIELD OF THE DISCLOSURE

The aim of the present invention is to overcome the drawbacks of the known products existing on the market, and in particular the use of products of animal origin and more particularly bovine origin, the obligation for regular injection (every few months), the appearance of allergic reactions, and the difficulty of an injection that is simple to perform.

SUMMARY OF THE DISCLOSURE

To do this, one of the embodiments of the invention uses a biodegradable thixotropic compound with pseudoplastic properties that may be used in an injectable implant according to the invention, which makes it possible to stabilize the suspension and to appreciably facilitate the injection of any material, whether or not biodegradable, facilitating the manufacture of said implant and the syringeability of said implant through fine needles, typically of 25 to 30 gauge, which are preferable for dermatological and/or esthetic use.

Another of the embodiments of the invention uses a resorbable ceramic compound chosen for its harmlessness and already widely used in the medical field, more particularly in the field of bone tissue implants.

The family of patents and/or patent applications including patent EP-B1-0 627 899 is already known, which patent describes an injectable implant composition comprising a biocompatible ceramic matrix present in a pharmaceutically acceptable fluid support chosen from the group consisting of a buffered aqueous medium, biocompatible organic polymers that dissipate from a site of injection into a tissue, and mixtures thereof, in which the ceramic matrix comprises particles with a size distribution included in the range from 50 μm to 250 μm. The implant of said patent is intended to fill fibrous cavities, mainly close to bone tissue or hard tissue. Although it is mentioned that the implant described can be injected into soft tissues, with needles with a gauge of greater than 20, preferably greater than 22, it is, however (and contradictorily), also indicated that this injection, which should aid the growth of tissues, should preferably be performed with a needle of gauge 20 or less, and close to bone or cartilage for the purpose of nasal repair or sphincter repair. Moreover, it is clearly specified that the size of the ceramics, from 50 μm to 250 μm and preferably from 100 μm to 200 μm, should allow injection with fine needles. Below a size of 50 μm, it is indicated that the ceramic particles will have the drawback of being subject to excessive phagocytosis. Above 200 μm, it is indicated that the particles will be too difficult to inject. In the implementation example, the implants injected, and analyzed, comprise hydroxyapatite (HA) mixed with collagen. They all show a start of calcification. Another example does not comprise ceramic alone. Specifically, it is clearly stated in the preamble of the patent that collagen acts for filling under the surface of the skin, whereas the ceramic particles are intended for repairs close to bones and cartilage. However, the presence of collagen is not desired, as has been explained above.

The documents from Hubbard William G such as WO-A-93/15721 and from Bioform Inc. such as WO-A-01/12247 and EP-A-1 080 698 are also known. They describe biocompatible and permanent, i.e. nonresorbable, materials comprising a matrix of ceramic particles, for increasing the volume of soft tissue. Said particles are substantially spherical and have a controlled size, generally of 35 to 150 μm, but it is also possible for this size to be less than 35 μm, preferably from 10 to 30 μm. In WO-A-93/15721 and WO-A-01/12247, a preferred ceramic material is hydroxyapatite or HAP, but tricalcium phosphate may also be used. The vehicle for these particles is a resorbable, biocompatible lubricant material comprising a polysaccharide. In WO-A-93/15721, among the possible polysaccharides mentioned are sodium carboxymethylcellulose (CMC) and glycerol, a combination thereof being particularly preferred. In WO-A-01/12247, among the possible polysaccharides mentioned are hyaluronic acid, but above all sodium carboxymethylcellulose (CMC) and glycerol, a combination thereof being particularly preferred. The essential difference between these implants and those of the present invention lies in the permanent nature of the implants according to this prior art.

The injectable implants according to the invention overcome the drawbacks of the prior art. They in particular make it possible to fill wrinkles, fine lines, scars and/or skin depressions with a simple and effective product that is almost totally bioresorbable.

DETAILED DESCRIPTION OF THE DISCLOSURE

The invention relates firstly to a use in an implant for subcutaneous or intradermal injection into fibrous tissue of at least one biodegradable thixotropic compound with pseudoplastic properties, preferably at least one bioresorbable thixotropic compound with pseudoplastic properties, and even more preferably at least one thixotropic compound with pseudoplastic properties based on xanthan gum.

Such a biodegradable thixotropic compound with pseudoplastic properties that may be used in an injectable implant according to the invention makes it possible to stabilize the suspension and to appreciably facilitate the injection of any material, which may or may not be biodegradable, facilitating the manufacture of said implant and the syringeability of said implant through fine needles, typically of gauge 25 to 30, which are preferable for dermatological and/or esthetic use.

The invention also relates, secondly, to an implant for subcutaneous or intradermal injection into fibrous tissue, comprising at least one biodegradable thixotropic compound with pseudoplastic properties, preferably at least one bioresorbable thixotropic compound with pseudoplastic properties, and even more preferably at least one thixotropic compound with pseudoplastic properties based on xanthan gum.

The invention relates in particular to one embodiment of said implant, which is an implant for subcutaneous or intradermal injection into fibrous tissue, comprising microparticles of at least one biocompatible ceramic compound in suspension in at least one vector fluid, said implant being characterized in that said microparticles are biodegradable, preferably bioresorbable, and have a size of from 10 to 80 μm, preferably from 10 to 50 μm, more preferably from 10 to 45 μm and even more preferably from 15 to 40 μm, said ceramic compound comprising at least one component chosen from the group formed by tricalcium phosphate (βTCP) and biphasic products (BPC), which comprise HAP and βTCP in variable proportion, said component preferably being βTCP, and in that said vector fluid comprises at least one compound based on hyaluronic acid and at least one biodegradable thixotropic compound with pseudoplastic properties, preferably at least one bioresorbable thixotropic compound with pseudoplastic properties and even more preferably at least one thixotropic compound with pseudoplastic properties based on xanthan gum.

According to the invention, the term "implant" means either a composition intended to be implanted or a composition that has been implanted into the human or animal body. According to the invention, the term "vector fluid" means a compound that conveys the ceramic compound, and that is in fluid form. The term "fluid" also means herein a gel, for example a viscoelastic gel. According to the invention, the term "gel" means a three-dimensional physical structure with viscosifying, rheological and thixotropic properties. Such a gel thus comprises the presence of at least one thixotropic compound with pseudoplastic properties. According to the invention, the term "fibrous tissue" means a subcutaneous space of essentially fibrous nature, capable of being filled with fibers. According to the invention, the term "subcutaneous" means hypodermic, i.e. under the dermis. According to the invention, the term "intradermal" means in the thickness of the dermis. According to the invention, the term "in suspension" means in the form of a powder dispersed in a fluid and insoluble in said fluid.

According to the invention, the term "biodegradation" or "degradation" means decomposition in a biological environment of a material resulting from a cellular, enzymatic, bacterial or viral activity. The biodegradation corresponds to the loss of the physical properties. According to the invention, the term "bioresorption" or "resorption" means a biodegradation that results in the complete disappearance of the material, the degradation products generally being removed via the kidneys or metabolized.

The implant according to the invention, whether or not in its preferred embodiment, comprises at least one biodegradable thixotropic compound with pseudoplastic properties, preferably at least one bioresorbable thixotropic compound with pseudoplastic properties and even more preferably at least one thixotropic compound with pseudoplastic properties based on xanthan gum. For example, such a compound is Xanthural 180® from the company CPKELCO Inc.

In the preferred embodiment of the implant according to the invention, the microparticles of ceramic compound are generally resorbable (or virtually resorbable), once the implantation has been made into the fibrous tissue, within a period of 2 to 36 months, preferably from 3 to 24 months and even more preferably from 4 to 18 months. It is thus referred to as a resorbable ceramic. Needless to say, the vector fluid is chosen such that it is itself biodegradable and preferably bioresorbable, and also compatible with the resorbability properties of the ceramic compound. In any case, care will generally be taken, according to the invention, to avoid vectors of animal origin such as bovine collagen.

The size of the microparticles is a mean size, measured by screening (typically by a method via suction and vibration using a standardized screen according to AFNOR) or by laser granulometry. The error percentages are approximately and generally about 10% by screening and about 2% by laser granulometry. Preferably, the microparticles generally have a size of between 10 and 80 µm and preferably from 10 to 50 µm. Even more preferably, the microparticles have a size of from 10 to 45 µm and preferably from 15 to 40 µm.

Any form of microparticles is included in the context of the present invention. According to one variant, the microparticles may be substantially microspheres.

According to the invention, the term "microparticles" means microparticles that may or may not be coated with a biocompatible excipient known to those skilled in the art.

Thus, according to the invention, the resorbable ceramic microparticles are a material that is neither organic nor metallic, which has generally undergone a curing treatment at temperature and pressure (sintering). The general structure of the ceramics is biphasic: vitreous phase (matrix) and crystalline phase (crystallized needles). Conventional ceramics are generally terracotta products, porcelains, earthenware, glasses, etc. The novel ceramics, which are more advantageous in the context of the invention, have in common advantageous properties such as high corrosion resistance, mechanical qualities for dense ceramics, and electrical and ionic properties for industrial use. Different families of ceramics exist as a function of their composition, including calcium phosphates, which are bioactive ceramics.

The implantation of the injectable implant into the body essentially has the aim of generating a tissue of new collagen fibers, which is generally termed neo-collagenesis, which is responsible for the filling of the fine line or the skin depression. The operation followed is to start the mechanism, i.e. the synthesis of new collagen fibers, but without the implant remaining in the body for too long. Specifically, any implanted foreign body induces a nonspecific foreign body inflammatory reaction, which, in this indication, is desired in the medium term. The choice of a ceramic compound that has a duration of resorbability as defined above advantageously makes it possible to combine maximum efficacy with minimum risk.

Specifically, no nonresorbable implant appears to be generally desirable. Thus, advantageously according to the invention, the ceramic compound that constitutes a mineral phase degrades or dissolves almost totally after subcutaneous or intradermal injection and is then almost totally removed from the body by the natural processes.

In addition, the implant according to the invention advantageously combines the ease of use, the syringeability of the product, the resorbability over a controlled period of the vector and of the ceramic compound, the absence of allergenicity of the product (due to the absence of compounds of animal origin), which makes any preliminary testing unnecessary.

According to the invention, the ceramic compound generally has a specific surface area of from 0.5 m$^2$/g to 100 m$^2$/g and preferably from 2 m$^2$/g to 27 m$^2$/g. The specific surface area is generally measured by the BET method.

The invention also relates to an injectable implant such that the microparticles are present in the vector fluid in a weight/volume proportion strictly greater than 0% and less than 15%, and preferably from 2% to 12%.

According to the invention, the ceramic compound generally comprises at least one component chosen from the group formed by tricalcium phosphate (βTCP) and biphasic products (BPC) comprising hydroxyapatite (HAP) and βTCP in variable proportion, said component preferably being βTCP, on condition that said microparticles are biodegradable, and preferably bioresorbable. Thus, HAP microparticles are excluded according to the invention.

Hydroxyapatite (HAP), of general formula $Ca_{10}(PO_4)_6(OH)_2$, is the closest to biological apatite crystals. The Ca/P atomic ratio (1.67) is generally less than that of bone. Tricalcium phosphate (βTCP) has the formula $Ca_3(PO_4)_2$. The Ca/P ratio is generally 1.5. The biphasic products (BPC) combine in a variable ratio HAP and βTCP. It should be noted that the preparation of these products generally involves many variables that condition their biological behavior: elemental composition, nature of the mineral phases, micro- and macroporosity, presence of impurities.

In this particularly preferred embodiment according to the invention, the ceramic compound according to the invention is bioactive, and thus has chemical exchanges with living tissues. According to the invention, the term "bioactivity" means a property allowing specific chemical reactions, at the implant-receptor tissue interface. It depends directly on the chemical and physicochemical properties of the material, and is opposite to bioinertia (property of biocompatible but inert materials). After implantation by injection, the compound is generally the site of an extracellular dissolution and a degradation of cellular origin, depending on the chemical structure (βTCP, BCP), the physical structure (pores of the material) and the environment of the material. The biological fluids, including the vector fluid, occupying the micropores of the ceramic compound become enriched in calcium. The degradation, which is preferably a resorption of the implant according to the invention, should generally not be too fast to allow a nonspecific foreign body inflammatory reaction responsible for the synthesis of new collagen fibers. HAP is sparingly soluble and its rate of degradation is generally very low in vivo, but varies as a function of the pH. βTCP is much more soluble and generally has a high in vivo degradation. The biphasic products have properties that vary as a function of the ratio between HAP and βTCP. The result of the implantation thus depends usually on the colonization and resorption kinetics, which are generally conditioned by the chemical and physicochemical characteristics of the injectable implant according to the invention; advantageously, these criteria are controlled by means of the nature of the implant according to the invention.

For example, the ceramic microparticles are Biosorb® particles from the company, sold as βTCP particles by the company SBM.

The vector fluid generally has limited resorbability, typically from about one to about four months.

Preferably, the vector fluid of the implant is a biocompatible gel and preferably a bioresorbable gel.

In one preferred embodiment of the invention, the vector fluid is such that the hyaluronic acid-based compound predominantly comprises hyaluronic acid. According to the invention, the term "-based" means that at least the majority of said compound is hyaluronic acid, crosslinked or non-crosslinked, or a salt thereof or a polysaccharide derivative thereof.

In one preferred embodiment of the invention, said hyaluronic acid-based compound comprises hyaluronic acid with a molecular mass of greater than one million daltons and preferably from one million to five million daltons.

The vector fluid may also additionally comprise at least one component chosen from the group formed by cellulose derivatives such as CMC (carboxymethylcellulose), HPMC (hydroxypropylmethylcellulose) or HPC (hydroxypropylcellulose) and glycosaminoglycans other than hyaluronic acid.

The implant according to the invention is in the form of microparticles, optionally in the form of microspheres, in suspension in a vector fluid conveying said microparticles. These microparticles should have a diameter of greater than 10 µm, in order to avoid rapid or immediate phagocytosis by macrophages. They should have a diameter of less than 45 µm, so as to be able to be injected with a very fine needle (typically from gauge 25 to gauge 30). Advantageously and according to the invention, the vector fluid is chosen so as to have an intrinsic viscosity that is sufficient to be injected through a needle of gauge 25 to 30, for example from 1500 to 4000 m$^3$/kg at 25° C., and so as to keep the mineral phase homogeneous, said phase being the ceramic compound in suspension in the fluid phase, which is the vector fluid.

The ceramic compound according to the invention may be prepared according to any process known to those skilled in the art. Two types of process may be distinguished, depending on whether the ceramic compound is of synthetic or natural (biological) origin. The preparation of the first type of process, for the ceramic compound of synthetic origin, is as described below. The base products are prepared by chemical synthesis and are in powder form. The forming for use in subcutaneous or intradermal injection (porosity and form) requires various operations after calcination, at a temperature generally below 900° C. Thus, the powder may be compacted under pressure and then heated, to a temperature generally from 1100 to 1500° C., which at least partially produces sintering of the constituents of the powder. Fusion of said constituents then takes place, followed by aggregation of the microcrystals that are formed on cooling and remain welded. The interstices between these microparticles determine a microporosity, i.e. a micro-particle size at least partially of a size generally less than 5 µm. The microporosity depends on both the pressure and the temperature. The addition to the powder of, for example, naphthalene beads may advantageously create a macroporosity, i.e. a micro-particle size at least partially greater generally than 100 µm. The diameter of the macropores is determined by the diameter of said beads, which sublime at high temperature.

As regards the preparation of the second type of process, for the ceramic compound of natural origin, it is generally as described above for the first type of preparation, i.e. according to an identical heat treatment, but starting with biological structures that are usually preexisting porous phosphocalcic structures (coral or bone). Said heat treatment destroys the organic components and causes ceramization of the phosphocalcic framework.

The physicochemical characterization of the ceramic compound according to the invention is generally as known to those skilled in the art. It may be performed by elemental analysis, for example by assaying (of the calcium (Ca), the phosphorus (P) and the trace element(s)), by investigation of the heavy element(s) possibly present (pollution) and/or by determination of the Ca/P ratio. It may also be performed, in addition or otherwise to elemental analysis, by X-ray diffraction, for example by determination of the mineral phases (HAP, βTCP), by determination of the crystallinity (size or shape of the crystals) and/or by investigation of crystal defects. It may also be performed, in addition or otherwise to elemental analysis and/or X-ray diffraction, by infrared spectrometry, for example by determination of functional groups (carbonates, presence of water, organic components, ionic substitutions, etc.), by structure determination (determination of the surface states or of the micro- and macroporosity).

The invention also relates to a process for preparing an injectable implant according to the invention, comprising the following steps:

a biocompatible ceramic compound in the form of microparticles as defined above is prepared in a preliminary step, in another step, independently of the above preliminary step, a solution of a vector fluid comprising at least one hyaluronic acid-based compound and at least one biodegradable thixotropic compound with pseudoplastic properties is prepared, the ceramic compound from the preliminary step is then introduced into the vector fluid from the other step, in a final step, so as to obtain an essentially homogeneous suspension, typically by using a homogenization means of mixer type.

According to the invention, the term "solution of a vector fluid" means a mixture of a vector fluid optionally in a solvent, preferably an aqueous solvent.

The injectable implant according to the invention may be in the form of a ready-to-use prefilled syringe, a ready-to-use prefilled bottle, or a lyophilizate to be reconstituted extemporaneously.

The invention also relates to a kit for the extemporaneous use of an implant according to the invention, such that it comprises at least one biocompatible ceramic compound and at least one vector fluid.

The kit according to the invention generally comprises the ceramic compound in a first part and the vector in a second part, and thus allows the reconstitution of the injectable implant according to the invention during its use.

The invention relates to the use of an injectable implant according to the invention for filling wrinkles and/or fine lines and/or skin depressions and/or scars, comprising the subcutaneous injection of such an implant. This applies to either the human body or the animal body. Such a use thus mainly lies in the field of reparatory or plastic surgery, or in the field of esthetic dermatology.

EXAMPLES

The various compounds given as examples included in the formulation of our products are the following:
βTCP
Sodium hyaluronate
Xanthan They have been chosen for their resorbable nature and their thickening and stabilizing properties in suspensions.

Examples of Formulations

| | | | |
|---|---|---|---|
| βTCP | 10% (W/V) | βTCP | 7% (W/V) |
| Sodium hyaluronate | 2% | Sodium hyaluronate | 2.2% |
| Xanthan | 0.5% | Xanthan | 0.5% |
| βTCP | 10% (W/V) | βTCP | 7% (W/V) |
| Sodium hyaluronate | 2.2% | Sodium hyaluronate | 2.2% |
| Xanthan | 0.6% | Xanthan | 0.6% |
| βTCP | 10% (W/V) | βTCP | 7% (W/V) |

| | | | |
|---|---|---|---|
| Sodium hyaluronate | 1.8% | Sodium hyaluronate | 1.8% |
| Xanthan | 1% | Xanthan | 1% |
| βTCP | 10% (W/V) | βTCP | 7% (W/V) |
| Sodium hyaluronate | 1.6% | Sodium hyaluronate | 1.6% |
| Xanthan | 0.8% | Xanthan | 0.8% |

The ceramic microparticles that have been used in these examples are Biosorb® particles from the company, sold as βTCP particles by the company SBM.

They are fully tolerated and thus biocompatible.

The cytotoxicity, sensitization, irritation and implantation studies in animals according to ISO standard 10993 demonstrate excellent tolerance of the formulations given as examples according to the invention. A study of acute toxicity by intraperitoneal injection demonstrated that the lethal dose in mice is greater than 10 mL/kg; the test product, (βTCP in suspension in a gel of hyaluronic acid and xanthan) shows no toxicity and satisfies the test in accordance with ISO standard 10993.

Unlike bioinert ceramics (alumina, zirconia), βTCP is a bioactive ceramic, and thus undergoes chemical exchanges with living tissues.

Unlike hydroxyapatite (HAP), βTCP is much more soluble and shows high in vivo degradation.

The resorption of the implant according to the invention should not be too fast to allow colonization of the microparticles by macrophages. A nonspecific foreign body inflammatory reaction then begins, which results in encapsulation with fibrous tissue.

The clinical result thus depends on the colonization and resorption kinetics, which are conditioned by the chemical and physicochemical characteristics of the implant; these criteria should generally be perfectly controlled.

βTCP had not yet been evaluated in the filling of wrinkles (intradermal injection). However, many applications in soft tissues (periodonty, guided tissue regeneration) and in bone tissues have demonstrated the satisfactory tolerance of βTCP, both in animals and in man. Formulations for topical application have been tested in rats. This did not demonstrate any irritation or sensitization phenomenon.

After implantation, the material is the site of extracellular dissolution and degradation of cellular origin.

An implantation study in rats was conducted for 3 months to evaluate the effects of the formulations according to the invention in intradermal injection. These formulations showed the total harmlessness of the product during and after the injection (no pain and no irritation). A histological study demonstrated after subcutaneous implantation, after an interval of 3 months, no macroscopic lesion, irrespective of the βTCP concentrations used.

Nonspecific foreign body inflammatory reactions are observed in accordance with the literature data. Furthermore, these reactions, localized solely to contact with the material, demonstrate the total tolerance of the test product. No abscessing or tissue necrosis was observed around these implants.

At one month, a vascularized connective tissue capsule surrounding the implant is observed. This capsule consists mainly of connective cells, macrophages, lymphocytes, foreign-body giant cells and mastocytes.

At 3 months, a marked decrease in the cell density of the connective capsule and also in its thickness are noted, reflecting a decrease in the intensity of the inflammatory reaction gradually as the implant degrades (about 50% at 3 months, which proves that the product will have totally disappeared between 8 and 16 months according to the known degradation models). Only the number of mastocytes remains unchanged. On the other hand, an increase in the deposition of collagen fibers is noted.

Development Rationale

The various formulations were evaluated with and without xanthan and were then subjected to autoclaving cycles (121° C., 20 minutes) in order to evaluate the effect of xanthan on the suspension stabilization. Some of these preparations were formulated using water for injectable preparations, others using 0.9% sodium chloride solution in order to measure the effect of a saline solution on the viscosity of the gels prepared after a steam sterilization cycle. These studies revealed the very good suspension power of xanthan and also better heat resistance in the presence of a 0.9% concentrated saline solution. The current stability or prestability data documents confirm a stability of autoclaved suspensions prepared with 0.5% and 0.6% xanthan in a 2% hyaluronic acid gel.

Xanthan opposes the sedimentation of the dispersions on account of its very high flow threshold (or shear stress). This characteristic, and the induced viscosity, are very much higher than those for plant gums (guar gum or locust bean gum), grafted celluloses or alginates.

The fundamental property of xanthan is its action on controlling the rheology of aqueous systems and its stabilizing effect on aqueous multiphase systems, whether it is a matter of stabilizing a liquid (emulsions), a solid (suspensions) or a gas (foams).

The rheological behavior of xanthan moreover has the characteristic of high pseudoplasticity, i.e. reversible viscous behavior with respect to shear, which is higher than that of polysaccharides such as hyaluronic acid mentioned above.

It shows resistance to hydrolysis by enzymes, including galactomannanases, amylases, cellulases, pectinases, proteases, etc.

All these characteristics make xanthan an adjuvant of choice for the injectable formulations for esthetic and dermatological purposes.

We are claiming the use of xanthan for injectable preparations for esthetic and dermatological purposes and more generally as a formulation agent in injectable preparations in the field of human and animal medicine.

The invention claimed is:

1. A resorbable implant for subcutaneous or intradermal injection into fibrous tissue, comprising microparticles of one biocompatible ceramic compound in suspension in at least one vector fluid,
   wherein said microparticles are biodegradable, once the implantation has been made into the fibrous tissue, within a period of from 2 to 36 months and have a size of from 10 to 80 μm said ceramic compound is tricalcium phosphate (βTCP) and has a specific surface area of from 0.5 $m^2/g$ to 100 $m^2/g$, and said vector fluid comprises at least one compound based on hyaluronic acid and at least one biodegradable thixotropic compound with pseudoplastic properties.

2. The implant according to claim 1 wherein said microparticles have a size of from 15 to 50 μm.

3. The implant according to claim 1 wherein said vector fluid comprises at least one thixotropic compound with pseudoplastic properties based on xanthan gum.

4. The implant according to claim 1 wherein said vector fluid comprises at least one thixotropic compound with pseudoplastic properties based on cellulose derivatives.

5. The implant according to claim 4 wherein the cellulose derivatives are selected from the group consisting of carboxymethyl cellulose (CMC), hydroxypropylmethyl cellulose (HPMC) and hydroxypropyl cellulose (HPC).

6. The implant according to claim 5 wherein the cellulose derivative is a carboxymethyl cellulose (CMC).

7. The implant according to claim 1 wherein said ceramic compound has a specific surface area of from 2 m2/g to 27 m2/g.

8. The implant according to claim 1 wherein the microparticles are bioresorbable, once the implantation has been made into a fibrous tissue, within a period of from 3 to 24 months.

9. The implant according to claim 8 wherein the microparticles are bioresorbable, once the implantation has been made into a fibrous tissue, within a period of from 4 to 18 months.

10. The implant according to claim 1 wherein the microparticles are present in the vector fluid in a weight/volume proportion strictly greater than 0% and less than 15%.

11. The implant according to claim 1 wherein the microparticles are present in the vector fluid in a weight/volume proportion from 2% to 12%.

12. The implant according to claim 1 wherein the vector fluid for the implant is a biocompatible gel.

13. The implant according to claim 1 wherein the vector fluid for the implant is a bioresorbable gel.

14. The implant according to claim 1 wherein the hyaluronic acid-based compound predominantly comprises hyaluronic acid.

15. The implant according to claim 14 wherein said hyaluronic acid-based compound comprises hyaluronic acid with a molecular weight of greater than one million daltons.

16. The implant according to claim 15 wherein said hyaluronic acid-based compound comprises hyaluronic acid with a molecular weight of from one million to five million daltons.

17. The implant according to claim 1, wherein said implant is in the form of a ready-to-use prefilled syringe, a ready-to-use prefilled bottle or a lyophilizate to be reconstituted.

18. A resorbable implant for subcutaneous or intradermal injection into fibrous tissue, comprising microparticles of one biocompatible ceramic compound in suspension in at least one vector fluid,
wherein said microparticles are biodegradable, once the implantation has been made into the fibrous tissue, within a period of from 2 to 36 months, have a size of from 10 to 80 µm, and are present in the vector fluid in a weight/volume proportion strictly greater than 0% and less than 15%, said ceramic compound is tricalcium phosphate (βTCP), and
said vector fluid comprises at least one compound based on hyaluronic acid and at least one biodegradable thixotropic compound with pseudoplastic properties.

19. The implant according to claim 18 wherein the microparticles are present in the vector fluid in a weight/volume proportion from 2% to 12%.

20. The implant according to claim 18 wherein said microparticles have a size of from 15 to 50 µm.

21. The implant according to claim 18 wherein said vector fluid comprises at least one thixotropic compound with pseudoplastic properties based on xanthan gum.

22. The implant according to claim 18 wherein said vector fluid comprises at least one thixotropic compound with pseudoplastic properties based on cellulose derivatives.

23. The implant according to claim 22 wherein the cellulose derivatives are selected from the group consisting of carboxymethyl cellulose (CMC), hydroxypropylmethyl cellulose (HPMC) and hydroxypropyl cellulose (HPC).

24. The implant according to claim 23 wherein the cellulose derivative is a carboxymethyl cellulose (CMC).

25. The implant according to claim 18 wherein the microparticles are bioresorbable, once the implantation has been made into a fibrous tissue, within a period of from 3 to 24 months.

26. The implant according to claim 25 wherein the microparticles are bioresorbable, once the implantation has been made into a fibrous tissue, within a period of from 4 to 18 months.

27. The implant according to claim 18 wherein the vector fluid for the implant is a biocompatible gel.

28. The implant according to claim 18 wherein the vector fluid for the implant is a bioresorbable gel.

29. The implant according to claim 18 wherein the hyaluronic acid-based compound predominantly comprises hyaluronic acid.

30. The implant according to claim 29 wherein said hyaluronic acid-based compound comprises hyaluronic acid with a molecular weight of greater than one million daltons.

31. The implant according to claim 30 wherein said hyaluronic acid-based compound comprises hyaluronic acid with a molecular weight of from one million to five million daltons.

32. The implant according to claim 18, wherein said implant is in the form of a ready-to-use prefilled syringe, a ready-to-use prefilled bottle or a lyophilizate to be reconstituted.

33. The implant according to claim 1, wherein said microparticles are sized suitable for delivery through fine needles of 25 to 30 gauge.

34. The implant according to claim 1, wherein said microparticles have a size of from 10 to 45 µm.

35. The implant according to claim 34, wherein said microparticles have a size of from 15 to 40 µm.

36. The implant according to claim 1, wherein said ceramic compound does not comprise hydroxyapatite (HAP).

37. The implant according to claim 1, wherein the implant is formulated such that, once the implantation has been made into the fibrous tissue, any biological fluids including the vector fluid occupying micropores of the ceramic compound become enriched in calcium.

38. The implant according to claim 1, wherein the hyaluronic acid-based compound is hyaluronic acid, crosslinked or non-crosslinked, or a salt thereof or a polysaccharide derivative thereof.

39. The implant according to claim 1, wherein said vector fluid has an intrinsic viscosity sufficient to be injected through fine needles of 25 to 30 gauge.

40. The implant according to claim 39, wherein said vector fluid has an intrinsic viscosity of from 1500 to 4000 m$^3$/kg at 25° C.

41. The implant according to claim 1, comprising about 7% to about 10% w/v 13TCP, about 1.6% to about 2.2% w/v sodium hyaluronate, and about 0.5% to about 1% w/v xanthan.

42. The implant according to claim 18, wherein said microparticles are sized suitable for delivery through fine needles of 25 to 30 gauge.

43. The implant according to claim 18, wherein said microparticles have a size of from 10 to 45 µm.

44. The implant according to claim 43, wherein said microparticles have a size of from 15 to 40 µm.

45. The implant according to claim 18, wherein said ceramic compound does not comprise hydroxyapatite (HAP).

46. The implant according to claim 18, wherein the implant is formulated such that, once the implantation has been made into the fibrous tissue, any biological fluids including the vector fluid occupying micropores of the ceramic compound become enriched in calcium.

47. The implant according to claim 18, wherein the hyaluronic acid-based compound is hyaluronic acid, crosslinked or non-crosslinked, or a salt thereof or a polysaccharide derivative thereof.

48. The implant according to claim 18, wherein said vector fluid has an intrinsic viscosity sufficient to be injected through fine needles of 25 to 30 gauge.

49. The implant according to claim 48, wherein said vector fluid has an intrinsic viscosity of from 1500 to 4000 $m^3$/kg at 25° C.

50. The implant according to claim 18, comprising about 7% to about 10% w/v βTCP, about 1.6% to about 2.2% w/v sodium hyaluronate, and about 0.5% to about 1% w/v xanthan.

51. A process for filling wrinkles and/or fine lines and/or skin depressions and/or scars, comprising the subcutaneous injection of an implant as claimed in claim 1.

52. A process for preparing an injectable, resorbable implant for subcutaneous or intradermal injection into fibrous tissue, said implant comprising microparticles of at least one biocompatible ceramic compound in suspension in at least one vector fluid, said implant being such that said microparticles are biodegradable, once the implantation has been made into the fibrous tissue, within a period of from 2 to 36 months and have a size of from 10 to 80 μm, said ceramic compound is comprising at least one component chosen from the group formed by tricalcium phosphate (~TCP) and has a specific surface area of from 0.5 m2/g to 100 $m^2$/g and biphasic products (BPC) which comprise HAP and βTCP in variable proportion, and in that said vector fluid comprises at least one compound based on hyaluronic acid and at least one biodegradable thixotropic compound with pseudoplastic properties, wherein said process comprises the following steps: a biocompatible ceramic compound in the form of microparticles is prepared in a first step, in another step, independently or not of the above preliminary step, a solution of a vector fluid comprising at least one hyaluronic acid-based compound and at least one biodegradable thixotropic compound with pseudoplastic properties is prepared, the ceramic compound from the first step is then introduced into the vector fluid from the other step, in a final step, so as to obtain an essentially homogeneous suspension.

* * * * *